United States Patent [19]

Reissmueller et al.

[11] 4,305,401

[45] Dec. 15, 1981

[54] DIGITAL WATCH/INFRARED PLETHYSMOGRAPH HAVING A QUICK RELEASE REMOTE PULSE SENSOR HAVING A FINGER CUFF

[75] Inventors: Manfred W. Reissmueller, Orange; Rudolf F. Zurcher, Newport Beach, both of Calif.

[73] Assignee: Hughes Aircraft Company, Culver City, Calif.

[21] Appl. No.: 39,531

[22] Filed: May 16, 1979

[51] Int. Cl.³ .............................................. A61B 5/02
[52] U.S. Cl. .................................................. 128/690
[58] Field of Search ....................... 128/633, 687–690

[56] References Cited

U.S. PATENT DOCUMENTS

| | | | |
|---|---|---|---|
| 3,646,931 | 3/1972 | Phelps et al. | 128/689 |
| 3,742,938 | 7/1973 | Stern | 128/687 |
| 4,129,124 | 12/1978 | Thalmann | 128/690 |
| 4,163,447 | 8/1979 | Orr | 128/690 |
| 4,185,621 | 1/1980 | Morrow | 128/690 |

FOREIGN PATENT DOCUMENTS 671279 10/1963 Canada ............................... 128/690

OTHER PUBLICATIONS

Anon, "IR Sensor Built into Watch Measures the Wearer's PR", *Electronics* vol. 5, No. 9, Apr. 28, 1977 pp. 32, 34.

Anon, "LCD Watch Doubles as a Heart Monitor", *Electronics* Mar. 1, 1979 pp. 42–43.

*Primary Examiner*—Robert W. Michell
*Assistant Examiner*—Francis J. Jaworski
*Attorney, Agent, or Firm*—Lewis B. Sternfels; W. H. MacAllister

[57] ABSTRACT

A digital watch has a face mounted local pulse sensor unit which is coupled to infrared plethysmograph electronics within the watch. The local pulse sensor includes transmitter and receiver photodiodes connected to the electronics by a plurality of moveable contact fingers. A connector at one end of a flat cable is insertable into a slotted opening on the side of the local pulse sensor and between the contact fingers and the two local photodiodes to disconnect the photodiodes from the electronics. Simultaneously, a remote pulse sensor unit at the other end of the cable is electrically coupled to the contact fingers by the connector for enabling the wearer's pulse at his finger to be sensed. A loop about the connector end of the cable maintains the connector in position when inserted into the local pulse sensor receptacle. A cuff at the remote sensor end of the cable secures the sensor to a wearer's finger for pulse monitoring.

11 Claims, 9 Drawing Figures

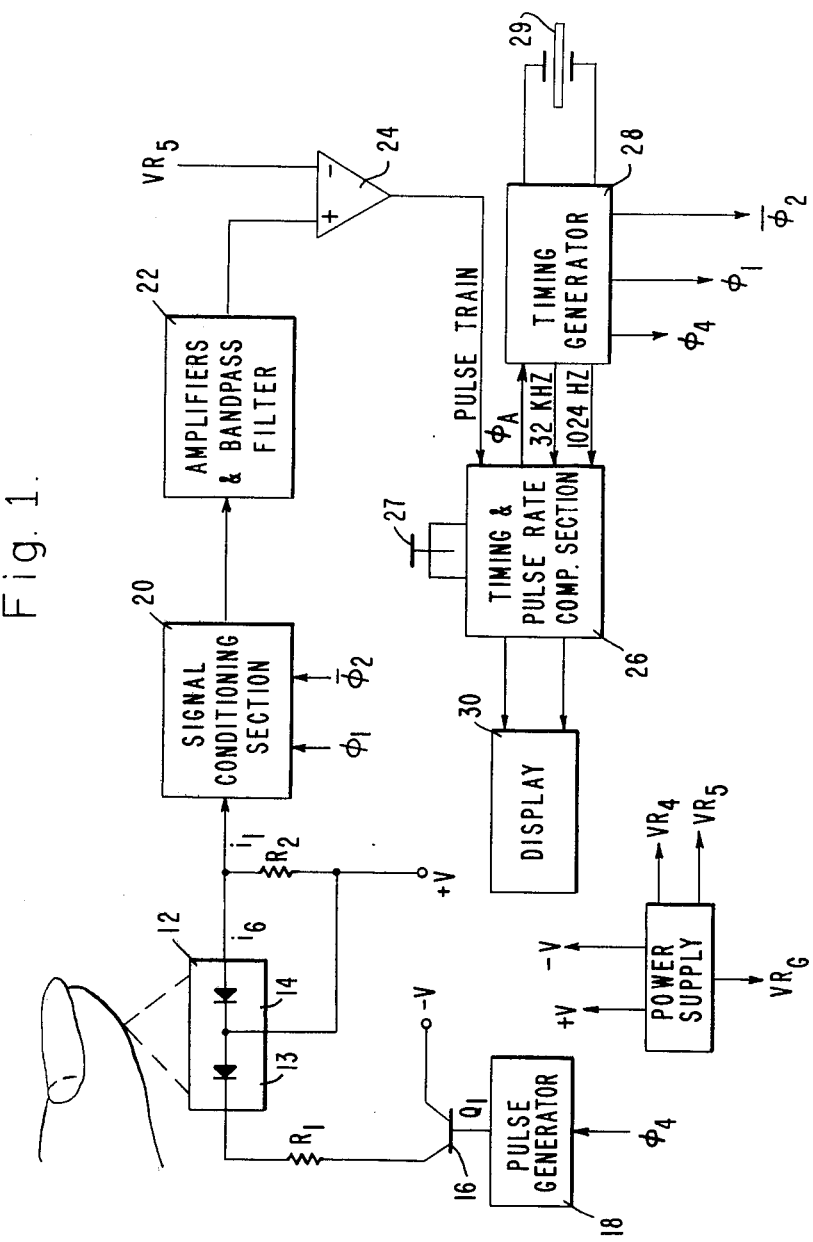

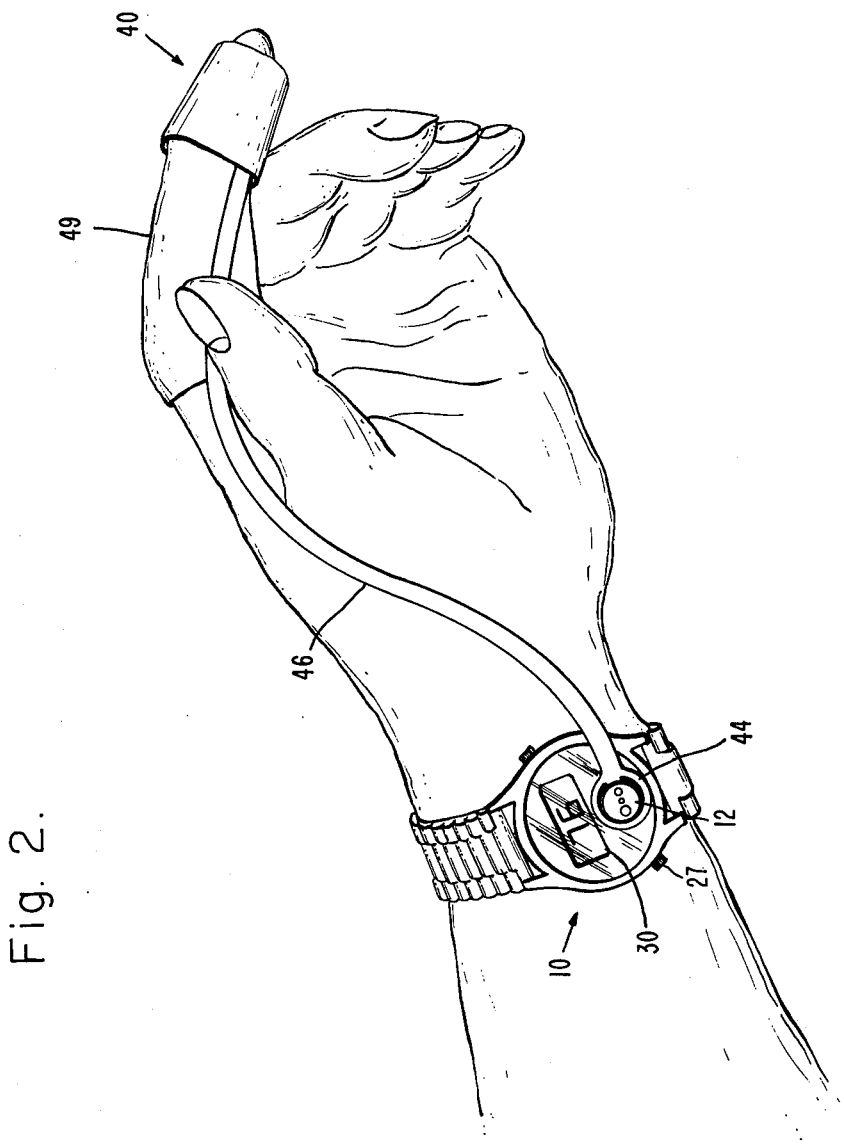

DIGITAL WATCH/INFRARED PLETHYSMOGRAPH HAVING A QUICK RELEASE REMOTE PULSE SENSOR HAVING A FINGER CUFF

BACKGROUND OF THE INVENTION

1. Field of the Invention

The invention relates generally to a digital watch having an infrared plethysmograph and, in prticular, to a remote pulse sensor cable for use with a pulse sensing digital watch.

2. Description of the Prior Art

Pulse sensing digital watches are relatively new to the field of heart rate monitoring but, nonetheless, their principles of operation are well known and understood. One of the first pulse sensing watches on the market utilizes an infrared pulse sensor mounted on a watch face and connected to special electronics within the watch. The wearer activates the plethysmograph electronics merely by pushing a button switch on the edge of the watch case, then placing his fingertip over the infrared sensor, and reading his pulse rate directly from the digital display.

Pulse rate sensing is dependent upon certain physiological changes which occur during each cardiac cycle, i.e., the diastole and the systole. In the diastole phase the cavities of the heart expand and fill with blood. The diastolic pressure is the lowest arterial blood pressure of a cardiac cycle occurring during the diastole of the heart. In the systole phase, the heart contracts, forcing the blood onward thus keeping the circulation up. The systolic pressure is the highest arterial pressure of a cardiac cycle. The fresh blood supply from the heart is conducted by arteries, and thence by capillaries. Veins return the blood supply to the heart. Blood in the arteries and capillaries is under pressure and flows in waves due to the beats of the heart. In response to the systole of the heart, the pressure in the arterial/capillary system increases to its maximum value and the system fills with the blood being pumped out of the heart. During diastole, the heart fills with blood from the veins as the pressure drops in the arterial/capillary system and the amount of blood in this system decreases.

One's finger tips contain a great number of these tiny capillaries which fill with a fresh blood supply during the systolic phase and empty during the diastolic phase. Heart-rate measurement relies on the slight increase in infrared light absorption by the blood in the capillaries of the fingertip during the systolic pressure wave.

An infrared plethysmograph within a digital watch may include a light emitting photodiode which emits either a continuous or a pulsed infrared signal which is directed at the capillaries in the fingertip. The IR reflected from the capillaries is detected by an infrared detector such as a photodiode or phototransistor. The IR detector is coupled to a microcomputer within the watch case. As explained above, the capillaries are more reflective of IR energy during the diastole than the systole. The microcomputer measures the differences in the signals reflected by the capillaries, counts the intervals between them, amplifies the data, averages the calculated heartbeat and displays it periodically after a predetermined number of heartbeats.

The reasons for wearing such a pulse sensing watch may be as varied as the number of individuals wearing them. But generally, persons are interested in knowing their pulse while at rest, to indicate their degree of relaxation, or during some activity, to determine, at least indirectly, the stress they place on their hearts. Sampling one's own pulse rate at rest is a simple procedure. The wearer merely turns the sensing electronics on, places his finger over the infrared sensor gently, and reads his pulse directly from the display. It is necessary to apply a constant and light finger pressure against the infrared sensor, otherwise false readings may occur. If too much pressure is applied, circulation through those capillaries may be severely curtailed and low pulse readings would result. If insufficient finger pressure is applied, the wearer's finger may move relative to the sensor thereby giving false readings.

In order for one to have a more accurate reading of one's pulse during an activity, the pulse should be read during that activity. Although a high heart-beat rate during a strenuous activity is not immediately reduced upon cessation of that activity, the heart does tend to slow down rapidly when the activity is terminated. Therefore, it is most desirable to sample one's pulse during the most strenuous phases for an accurate determination of the stress one places on one's heart.

Monitoring one's pulse in the course of some activities may be difficult because of the pressure requirements explained above. For example, a runner while running places a finger of his right hand on the wristwatch sensor worn on the left arm and hopes that he is applying the proper pressure. This is a rather clumsy and awkward attitude. More than likely the readings obtained would be inaccurate due to the pressure requirements. In order to obtain precise readings, that person would have to stop and take his pulse. However, when he stops, his heart has started its slowing process and the readings he obtains are not representative of his previously higher heartbeat.

OBJECTS AND SUMMARY OF THE INVENTION

Accordingly, it is an object of the present invention to provide a simple and reliable heartbeat monitoring system.

It is another object of the present invention to provide a pulse monitor having remote sensing.

It is yet another object of the present invention to provide a quick-release pulse sensor, cable and display operable with one hand.

It is still another object of the present invention to provide a pulse sensor and display for monitoring heartbeat during activities which require that both hands be free.

It is yet another object of the present invention to provide a remote pulse sensing device for applying a constant pressure for accurate pulse sensing.

It is another object of the present invention to provide a remote pulse sensing cable not requiring a detachable pulse sensor unit.

It is still another object of the present invention to provide a device for shielding a remote pulse sensor from ambient infrared signals.

In accordance with the foregoing objects, a quick release remote pulse sensing device includes a local pulse sensor unit connectable to infrared plethysmograph electronics. The local pulse sensor has a connector receptacle for receiving a remote pulse sensor cable which simultaneously disengages the local pulse sensor unit. The remote pulse sensor cable connector has a retainer at the connector end for maintaining the connector in place. A cuff applies the remote sensor unit to a wearer's finger for pulse monitoring.

BRIEF DESCRIPTION OF THE DRAWINGS

FIG. 1 is a schematic block diagram of an infrared plethsymograph.

FIG. 2 is a perspective view illustrating a pulse sensing watch and a remote sensor being worn.

DETAILED DESCRIPTION OF THE DRAWINGS

Figure 5:
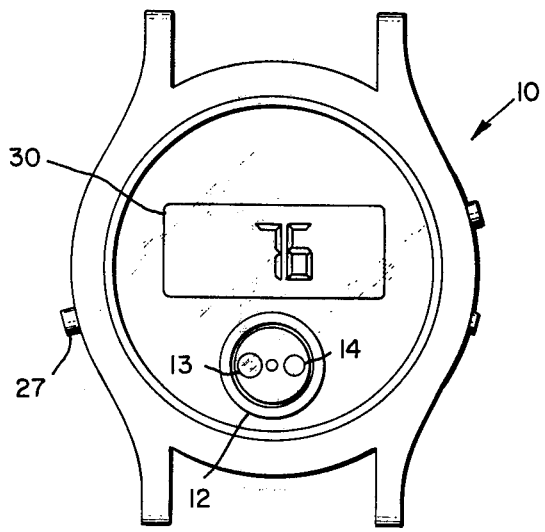
FIG. 5 is a plan view of the face of a pulse sensing digital watch.

FIG. 1 illustrates an infrared (IR) plethysmograph system as might be found in a digital watch 10 as depicted in FIGS. 2 and 5. A sensor 12 includes a light emitting photodiode 13 which transmits either a continuous wave IR signal or a pulsed IR signal. Another photodiode 14, which is situated next to the transmitting diode 13, receives the reflected IR energy. The transmitter 13 is powered by a transistor 16 which is controlled by a pulse generator 18. The transmitter 13 emits a pulsed infrared signal which is directed to the finger's capillaries beneath the skin. Depending on the phase of the pressure wave, either diastolic or systolic, the transmitter signal will be more or less reflected to the receiver 14. A signal conditioning section 20, directly coupled to the receiver 14, cancels asynchronous ambient light.

The signal conditioning section 20 is coupled directly to an amplifier and bandpass filter 22. The amplifier/filter 22 amplifies and filters the systolic pressure wave pulses which typically occur 60 to 80 per minute but which could easily double during periods of strenuous exercise, sometimes exceeding 200 pulses per minute. The amplifier/filter 22 in combination with the signal conditioning section 20 provides the pulse counting function for the system.

The output signal of the amplifier/filter 22 is provided to the positive input terminal of a voltage level discriminator 24. The discriminator 24 compares the input signal, at its positive input terminal, with a reference voltage $VR_5$, at its negative input terminal, which sets the detection level for the systolic pulses. A train of pulses representative of the heartbeat rate is transmitted to the digital watch timing and pulse rate computation section 26 which detects the time between the pulse edges such as the positive-going leading edges, of the systolic pulses in the train. It then computes the pulse rate. The type of computations provided by the section 26 is well known in the digital art and need not be explained in further detail. The pulse rate is then displayed as a decimal number by the digital watch's displays section 30.

A timing generator 28 responds to a crystal oscillator 29 and provides the timing $\phi_1$, $\bar{\phi}_2$ and $\phi_4$ as well as a 32 KHZ clock signal and a 1024 HZ signal to the computation section 26. The timing signals $\phi_1$ and $\bar{\phi}_2$ are applied to signal conditioning section 20 for providing carrier cancellation during the sampling pulse periods. The clock pulse signals $\phi_4$ are used to drive the transmitter 13 at a constant rate such as 73 HZ.

Depressing the push button switch 27 once, causes the timing and pulse rate computation section 26 to generate an analog power control signal $\phi_A$ which, in turn, causes the timing generator 28 to produce the timing and control signals which control the plethysmograph. Pressing the push button 27 a second time, causes the analog signal $\phi_A$ to be turned off, thus turning the pulse monitoring function off.

A more detailed discussion of an infrared plethysmograph may be found in copending applications Ser. Nos. 006,983 (now U.S. Pat. No. 4,260,951 issued Apr. 7, 1981) and 965,816 (now U.S. Pat. No. 4,258,719 issued Mar. 31, 1981) respectively entitles "Measurement System Having Pole Zero Cancellation" and "Heart Rate Measurement System" by Lanny L. Lewyn and assigned to the assignee of the present application.

Referring now more specifically to the invention, FIG. 2 illustrates an infrared plethysmograph digital watch 10 being worn by an individual. In the usual operation mode, i.e., without remote pulse sensing, the the wearer depresses the push button switch 27 to activate the plethysmograph electronics. He then places his finger over the pulse sensor unit 12 and the display 30 shows his pulse rate. The wearer may then depress the push button switch 27 a second time to turn the pulse sensing electronics off. This procedure would be followed in the case of the wearer being at rest or when his activity is such that he can occupy both hands for taking his pulse. However, when the wearer's activity is such that he must have one or both hands free, the remote pulse sensing cable arrangement 40 is used.

The remote pulse sensing cable arrangement 40 is connected into the connector receptacle (see FIGS. 6 and 7) on the side of the local pulse sensor unit 12. The pulse sensor unit 12 has a slotted opening 15 (See FIG. 6), parallel to the surface of the watch face, through which a spade-like connector 42 end (See FIGS. 4 and 7) of a printed circuit cable arrangement 40, is inserted. A loop 44, around the connector 42, is then slipped down over the pulse sensor unit 12 to hold the spade-like connector 42 in place. Inserting the connector 42 into the slot in the local pulse sensor unit 12 disengages the latter from the infrared electronics within and engages the remote sensor unit 48 (See FIG. 4) at the other end of the cable arrangement 40. The remote sensor unit 48 is held in place against the wearer's finger by a finger cuff 50. To operate the remote pulse sensing cable arrangement 40, the wearer merely depresses the push button switch 27 to activate the sensing electronics. The remote pulse sensor 48 transmits the infrared signals into the tissue and blood vessels of the wearer's finger which reflect variable amounts of the infrared energy. The electronics within the watch compute the pulse rate from the reflected signals as explained above.

The wearer may wish to shield the remote pulse sensor 48 from extraneous infrared signals and thus he would use a finger boot or shield 49 which is further described below in the next figure.

Using the remote pulse sensing cable arrangement 40 permits the wearer to sample his pulse during an activity which requires the freedom of both hands. Once the remote sensing cable 40 is plugged into the local pulse sensor unit 12 and worn on the finger, the wearer need only activate the plethysmograph system by pushing the button 27 once. A jogger, for instance, may sample his pulse while engaged in the activity, without being in the awkward position of jogging with his right hand locked onto the wrist of his left hand.

Figure 3:
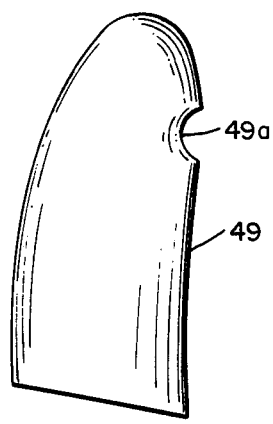
FIG. 3 is a side view of a finger shield.

Briefly, FIG. 3 illustrates the optional finger boot or shield 49 which may be utilized to shield the pulse sensor unit 48 from an ambient infrared interference light source. The boot 49 may be made of any suitable material which is opaque to infrared such as plastic or rubber, and has a circular opening 49a through which the sensor 48 is inserted. The necessity of additional shielding is determined by the particular sensors and electronics used. For example, the circuit of FIG. 1, provides for automatic cancellation of spurious signals and additional shielding may not be required.

Figure 4:
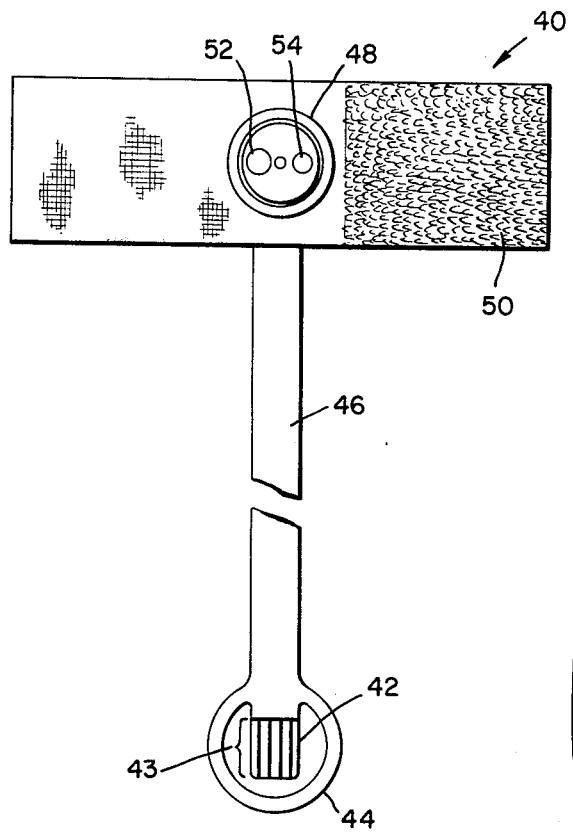
FIG. 4 is a plan view illustrating a remote pulse sensing cable according to the present invention.

The remote pulse sensing cable arrangement 40 according to FIG. 4 includes a flexible flat printed cable 46 having at least three flat wires. Each of the wires is 0.020 inch wide and each is separated by 0.020 inch from the other. A fourth wire may be used to provide electrical interference shielding around the signal wire from the receiver photodiode 14. The flexible cable 46 may be of the well-known type having a plurality of thin flat wires made of 1 oz. copper encased within a flat insulating material such as polyimide sold under the trade name Kapton. ® It is preferable, for safety purposes, to cover the flat cable 46 with two thin layers of Teflon ® fused together outside the width of the cable 46. Generally, most flexible cables tend to be somewhat stiff and have sharp edges. In order to prevent injury to the wearer from the sharp edges, the soft Teflon covering is added. The end of the cable forms the spade-like connector 42 which is insertable into the slotted receptacle on the side of the local pulse sensor 12. The connector 42 is made by removing the insulating material on one side of the cable from the area identified as 43. The loop 44 about the connector 42 is part of the cable 46. The inside diameter of the loop 44 is determined by the diameter of the pulse sensor unit 12. It is preferable to use the flexible flat printed cable because the end of the cable can function as the connector. A safety feature of flexible cable is that the loop 44 can break away if the cable should become entangled so as to prevent injury to the wearer. For example, if the cable 46 on a jogger's hand accidentally become entangled on a stationary object while jogging, the loop 44 would break, thus preventing injury. The cable 40 could still function without the loop 44, although it would not be as securely fastened to the local pulse sensor 12 as before.

The other end of the cable 46 has a remote pulse sensor unit 48, essentially identical to the local pulse sensor unit 12 except that it has no receptacle. The remote sensor 48 has transmitter and receiver photodiodes, 52 and 54, respectively, which are the same as the photodiodes 13 and 14 in the local pulse sensor unit 12. The remote pulse sensor unit 48 is situated in the middle of the finger cuff 50, which is used to apply the sensor 48 to the wearer's finger. The finger cuff 50, made of Velcro material, a trade name of Velcro U.S.A., Inc. is permanently fastened to the cable 46 and remote sensor unit 48 by a suitable adhesive. The Velcro cuff 50 permits easy one-hand application and removal of the remote sensor cable 40.

Referring now to FIG. 5, the digital watch 10 has a pulse sensor unit 12 situated on the watch face just below the display 30. The pulse sensor 12 includes the transmitter diode 13 and the receiver diode 14 both directed outwardly in a perpendicular direction to the plane of the watch face. Depressing the pulse sensor switch 27 activates the infrared detection electronics, causing the transmitter 13 to send an IR signal. The wearer places his finger over the sensor 12, and the receiver diode 14 receives the reflected IR from the capillaries in the wearer's finger. The return signal is processed by the electronics within the watch 10 and the pulse rate is periodically displayed on the display 30. For remote pulse sensing, the cable assembly 40 is plugged into the right side of the local sensor unit 12.

Figure 6:
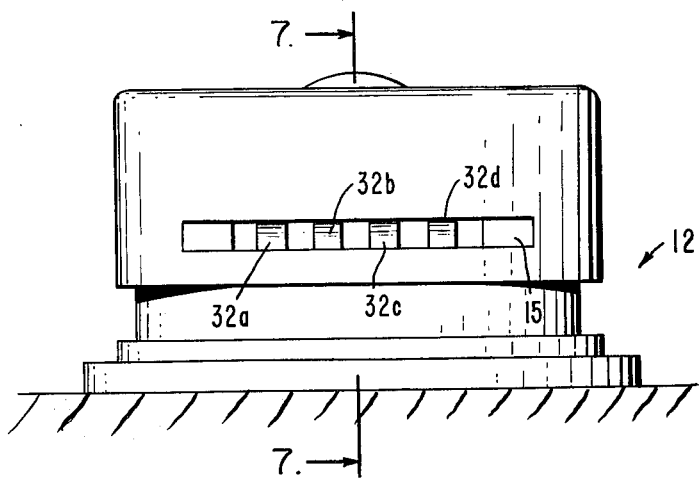
FIG. 6 is a side view of the pulse sensor unit.

FIG. 6 is a side view of the local pulse sensor unit 12, and illustrates the slotted opening 15 through which the cable connector 42 is inserted. The contact fingers 32a–32d are visible through the slotted opening.

Figure 7:
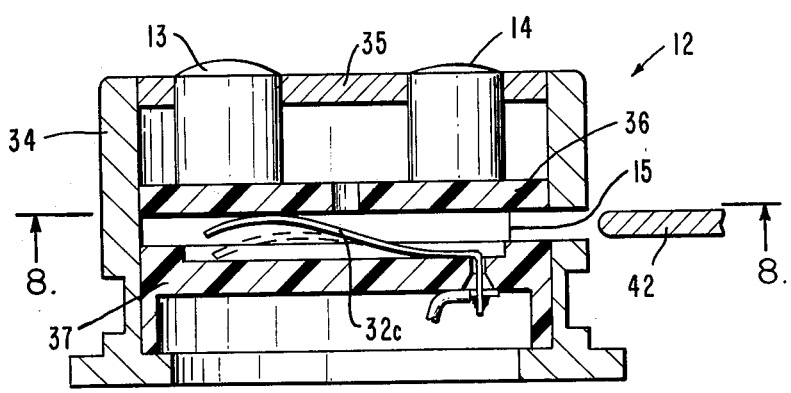
FIG. 7 is a cross-sectional view of the pulse sensor unit.

FIG. 7 is a cross-sectional view of the local pulse sensor unit 12. The barrel or housing 34 extends from inside the watch 10 to a distance approximately 0.120 inch above the watch's face. The transmitter and receiver diodes, 13 and 14 respectively, extend through a spacer 35 at the top of the housing 34. The photodiodes 13 and 14 are wired to one side of a printed circuit substrate 36. The substrate has plated through holes which connect with a series of four plated strips on the bottom side of the substrate 36. Four leaf spring contacts 32a–32d are mounted to a dielectric contact support member 37 and the top of the contacts are touching the printed strips on the substrate 36. Each of the leaf spring contacts is individually wired to its respective contact point within the plethysmograph electronics. As the cable connector 42 is inserted through the slot 15, the leaf spring contacts are pushed away from the contacts on the substrate 36. The connector wires then make contact with the leaf-spring contacts 32a–32d and the remote sensor unit 48 is ready for activation. The dashed outline of the leaf spring contact illustrates the folded down position of the contacts 32a–32d when the connector cable 42 is inserted through the slot 15.

Figure 8:
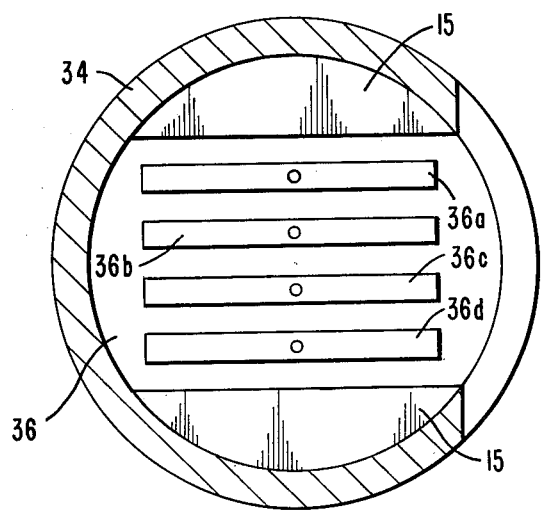
FIG. 8 is a plan view of the substrate to which the pulse sensing diodes are connected.

Referring briefly to FIG. 8, the contact side of the substrate 36 is illustrated in this cross-sectional view. The contacts 36a–36d are conductive copper strips, each being electrically connected to the opposite side of the substrate by plated through holes. The strips are sufficiently wide and spaced so that they make electrical connection with the leaf spring contact 32a–32d for conveying the signals between the sensor unit 12 and the plethysmograph electronics.

Figure 9:
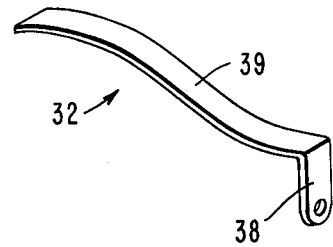
FIG. 9 is a perspective view illustrating a leaf spring contact finger.

A typical leaf spring contact 32 is illustrated in FIG. 9. The leaf spring contact 32 has a short straight arm 38 used to mount the contact 32 by inserting it through the support member 37. The long curved portion 39 of the contact 32 makes contact with the plated contacts on the substrate 36 or the cable connector 42.

In summary, what has been provided by the present invention is a quick-release, remote, pulse-sensing cable arrangement which utilizes a flexible flat printed cable having a remote pulse sensor unit at one end. The second end of the cable serves as a connector for inserting into a receptacle on the side of a local pulse sensor unit mounted on a digital watch. The local pulse sensor unit is simultaneously disengaged by the insertion of the connector as the remote sensor is engaged.

Although the present invention has been shown and described with reference to a particular embodiment, nevertheless, various changes and modifications obvious to one skilled in the art to which the invention pertains are deemed to be within the purview of the invention.

What is claimed is:

1. In an infrared plethysmograph having a remote pulse sensing feature having a mounting case, digital display pulse monitoring electronics mounted within said mounting case for computing and displaying a wearer's pulse rate, and a local pulse sensor unit in said mounting case and switchably coupled to said electronics, the improvement comprising a connector receptacle, means associated therewith disengageably coupling said local pulse sensor unit with said electronics, and a connector coupled to a remote pulse sensor unit and insertable within said receptacle and engageable with said means for disengaging said local pulse sensor unit from said electronics and for coupling said remote pulse sensor unit thereto.

2. The invention according to claim 1 wherein said mounting case comprises:
   a digital watch.

3. The invention according to claim 1 further comprising:
   a cable having said remote pulse sensor unit and said connector at opposed ends thereof.

4. The invention according to claim 3 further comprising:
   a cuff disposed about said remote sensor end of said cable for ensuring contact of said remote sensor with a wearer's finger.

5. The invention according to claim 3 further comprising:
   a finger boot opaque to infrared energy for shielding said remote pulse sensor unit from ambient infrared energy.

6. The invention according to claim 1 or 2 further comprising:
   retainer means positioned about said connector and engageable with said connector receptacle for maintaining said connector in contact with said electronics.

7. The invention according to claim 6 wherein said connector receptacle comprises a housing on said mounting case and said retainer means comprises a loop surrounding said connector and placeable about said housing for maintaining insertion of said connection within said receptacle.

8. The invention according to claim 1 wherein said disengageable coupling means comprises:
   conductive spring contact fingers coupled to said electronics and engageable with said local pulse sensor unit and being moveable therefrom by said connector.

9. The invention according to claim 8 further comprising a flat flexible cable having a plurality of parallel wires encased within insulation, and said connector comprises an exposed length of one side of said wires at one end of said cable making electrical contact with said conductive contact fingers and disengaging said local pulse sensor unit from said electronics.

10. The invention according to claim 8 wherein said pulse sensor unit includes pulse-sensing transmitting and receiving semiconductors and said connector receptacle comprises:
    a housing on said mounting case and supporting said semiconductors; and
    a conductor substrate disposed within said housing and having a plurality of conductive paths coupled to said semiconductors for contact with said conductive fingers.

11. The invention according to claim 1 wherein
    said connector receptacle comprises a housing on said mounting case, and
    said pulse sensor unit includes
        an infrared transmitting semiconductor disposed within said housing for directing an infrared signal outwardly from said housing toward a wearer and switchably connected to said electronics, and
        an infrared receiving semiconductor disposed within said housing for receiving a reflected infrared signal from said wearer and switchably connected to said electronics, and further including
    a plurality of conductive flat spring contact fingers disposed between said semiconductors and said electronics, for engaging and disengaging said semiconductors upon the insertion of said connector in said connector receptacle; and
    a remote pulse sensor cable having said connector and a remote pulse sensor at its opposed ends.

* * * * *